United States Patent [19]

Gittos et al.

[11] Patent Number: 4,696,927
[45] Date of Patent: Sep. 29, 1987

[54] 4-(2-PYRIMIDINYL)-1-PIPERAZINYL HETEROCYCLIC CARBONYL DERIVATIVES

[75] Inventors: Maurice W. Gittos, Plobsheim; Marcel Hibert, Strasbourg, both of France

[73] Assignee: Merrell Dow Pharmaceuticals Inc., Cincinnati, Ohio

[21] Appl. No.: 943,513

[22] Filed: Dec. 17, 1986

Related U.S. Application Data

[63] Continuation of Ser. No. 836,277, Mar. 5, 1986, abandoned.

[51] Int. Cl.$^4$ .............. A61K 31/505; A61K 31/535; C07D 413/14

[52] U.S. Cl. ..................... 514/236; 514/237; 514/252; 544/71; 544/96; 544/231; 544/296
[58] Field of Search ............... 544/71, 96, 231, 292; 514/236, 237, 252

[56] References Cited

FOREIGN PATENT DOCUMENTS 170213  2/1986  European Pat. Off. .

OTHER PUBLICATIONS

Peroutka, Biol. Psychiatry, [1985]; 20: 971-979.

Primary Examiner—Richard L. Raymond
Attorney, Agent, or Firm—Stephen L. Nesbitt

[57] ABSTRACT

This invention relates to 4-(2-pyrimidinyl)-1-piperazinyl heterocyclic carbonyl derivatives, to a process for their preparation, and to their use as anxiolytic agents.

8 Claims, No Drawings

4-(2-PYRIMIDINYL)-1-PIPERAZINYL HETEROCYCLIC CARBONYL DERIVATIVES

CROSS REFERENCE TO RELATED APPLICATION

This is a continuation of application Ser. No. 836,277, filed Mar. 5, 1986, now abandoned.

FIELD OF THE INVENTION

This invention relates to certain 4-(2-pyrimidinyl)-1-piperazinyl heterocyclic carbonyl derivatives and their use as anxiolytic agents.

BACKGROUND OF THE INVENTION

Anxiety has been defined as an apprehension or concern regarding some future event. Most, if not all, people occasionally suffer some symptoms of anxiety in response to appropriate stimuli. In some individuals, these feelings of anxiety or panic in response to the everyday pressures of life can be overwhelming, rendering the individual an unproductive member of society. Whereas individual group counseling represents the preferred primary mode of therapy, the use of chemotherapeutic agents has proven to be a useful adjunct in the treatment of anxiety, thereby enabling a seriously afflicted individual to regain productive status while undergoing concurrent psychotherapy.

Compounds of the class of benzodiazepines are currently the therapeutic agents of choice in the treatment of anxiety. In particular, chlordiazepoxide, diazepam and oxazepam are commonly used. This class of compounds has a great potential for misuse, particularly among the class of patients undergoing therapy. Moreover, the benzodiazepines generally possess undesired sedative effects and process detracting interactions with other drugs, including for example, alcohol.

Applicants have now discovered a class of novel 4-(2-pyrimidinyl)-1-piperazinyl heterocyclic carbonyl derivatives, which are useful as antianxiety agents, and which are generally free from the undesirable effects of the benzodiazepines. The compounds disclosed herein, when practiced in accordance with the teachings of this invention help to alleviate such symptoms as excessive fear, worry, restlessness, tension, stress, neurotic depression and are useful in the relief of some personality disorders.

SUMMARY OF THE INVENTION

This invention is directed to a class of 4-(2-pyrimidinyl)-1-piperazinyl heterocyclic carbonyl derivatives having the formula

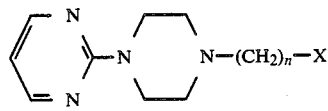
(1)

wherein n is an integer from 2 to 5; X is the radical

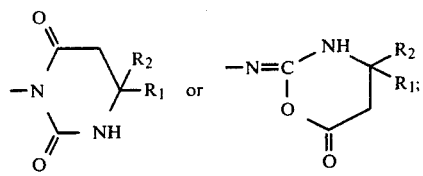

$R_1$ and $R_2$ are each methyl or when taken together form a tetramethylene or pentamethylene ring; and the pharmaceutically acceptable acid addition salts thereof.

This invention also relates to a process for the preparation of said compounds, pharmaceutical compositions thereof, and to the use of these compounds as anxiolytic agents.

DETAILED DESCRIPTION OF THE INVENTION

As used herein the term "pharmaceutically acceptable acid addition salts" is intended to apply to any non-toxic organic or inorganic acid addition salts of the base compounds represented by Formula I. Illustrative inorganic acids which form suitable salts include hydrochloric, hydrobromic, sulphuric and phosphoric acid and acid metal salts such as sodium monohydrogen orthophosphate and potassium hydrogen sulfate. Organic acids which form suitable salts include the mono, di and tricarboxylic acids. Illustrative examples of such acids include: acetic, glycolic, lactic, pyruvic, malonic, succinic, glutaric, fumaric, malic, tartaric, citric, ascorbic, maleic, hydroxymaleic, benzoic, p-hydroxybenzoic, phenylacetic, cinnamic, salicylic, 2-phenoxybenzoic acids, and sulfonic acids, such as methanesulfonic acid or 2-hydroxyethanesulfonic acid. Either the mono or the di-acid salts can be formed, and such salts can exist in either a hydrated or a substantially anhydrous form. In general, the acid addition salts of these compounds are crystalline materials which are soluble in water and in various hydrophilic organic solvents. In comparison to their free base forms, such salts generally demonstrate higher melting points and an increase in chemical stability.

As can be seen in formula (1) above, the compounds of this invention consist essentially of two terminal heterocyclic moieties separated by an alkylene chain having from 2 to 5 carbon atoms. More particularly, one such heterocyclic moiety consists of the 4-(2-pyrimidinyl)-1-piperazinyl group, whereas the other heterocyclic moiety represents either a substituted tetrahydro-pyrimidine-2,4-dione or a tetrahydro-6H-1,3-oxazine-6-one.

Still more particularly the compounds of this invention fall into two specific and distinct subclasses that can be illustrated as follows:

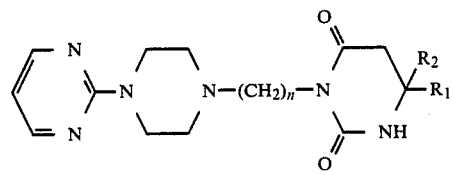

1-[ω-[4-(2-pyrimidinyl)-1-piperazinyl]alkyl]tetrahydropyrimidine-2,4-diones, and (1a)

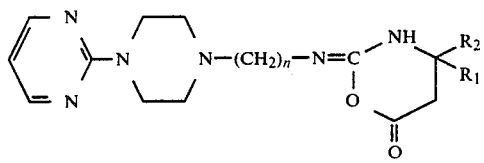

2-[ω-[4-(2-pyrimidinyl)-1-piperazinyl]alkylimino]tetrahydro-6H-1,3-oxazin-6-ones (1b)

Those alkylene groups in which the symbol n is from 2–4 carbon atoms represent the preferred alkylene chain lengths. The symbols $R_1$ and $R_2$ are either methyl or when taken together can form a tetramethylene or pentamethylene ring, i.e., either a cyclopentane or a cyclohexane ring.

The compounds of formula (1a) and (1b) are prepared via the same reaction procedure. That is to say, both the tetrahydro-pyrimidine-2,4-diones of formula (1a) and the tetrahydro-6H-1,3-oxazine-6-ones of formula (1b) are obtained from the same reaction mixture.

Thus, an alkyl ester of 3-[(N-alkyl)ureido]propionic acid (2) is condensed with the compound 1(2-pyrimidinyl)piperazine (3) to form an alkyl ester of 3-[N-[ω-[4-(2-pyrimidinyl)-1-piperazinyl]alkyl]ureido]-propionic acid (4). These alkyl esters (4) are generally not isolated, but are permitted to spontaneously cyclize to form the desired 1-[ω-[4-(2-pyrimidinyl)-1-piperazinyl]alkyl]-tetrahydro-pyrimidine-2,4-diones (1a) and 2-[ω-[4-(2-pyrimidinyl)-1-piperazinyl]alkylimino]tetrahydro-6H-1,3-oxazine-6-ones (1b). This reaction sequence can be illustrated as follows, wherein the symbols n, $R_1$ and $R_2$ are as previously described, R is a lower alkyl group and Y represents an appropriate leaving group.

atoms. Illustrative lower alkyl groups include methyl, ethyl, propyl, isopropyl, butyl and sec butyl. The term "leaving group", as indicated by the symbol Y, represents chlorine, bromine, iodine or the tosylate and mesylate groups.

The nucleophilic condensation is preferably conducted using equimolar amounts of 1-(2-pyrimidinyl)-piperazine (3) with the alkyl ester of 3-[(N-alkyl)ureido]propionic acid (2) for a period of from about 1 hour to 24 hours depending upon the particular reactants employed. The reaction temperature can range from about 25° C. to 140° C. Preferably the reaction is conducted at a temperature ranging from 60° C. to 125° C.

The use of solvents is preferred. Suitable solvents include any non-reactive solvent, preferably a polar solvent which has a boiling point in the range of from 60° C. to 150° C. Solvents which can be suitably employed include chlorinated hydrocarbons, such as ethylene chloride, methylene chloride or chloroform; chlorinated aromatic compounds such as 1,2,4-trichlorobenzene, or o-dichlorobenzene; ethereal solvents such as tetrahydrofuran or p-dioxane; aromatic solvents, such as benzene, toluene or xylene; or alcoholic solvents such as ethanol or butanol. Especially preferred solvents are those which are known to promote nucleophilic reactions, such as dimethylsulfoxide and dimethylformamide.

As indicated above, the alkyl esters (4) can cyclize spontaneously to form the desired compounds (1a) and (1b). This cyclization is enhanced by the presence of a catalytic quantity of a strong base, such as sodium or potassium tert-butoxide and in the presence of a polar solvent such as dimethylsulfoxide or dimethylformamide. The isomers (1a) and (1b) are obtained approximately in equimolecular amounts. Variations in reaction conditions can alter this ratio to favor one or the other isomer.

The alkyl esters of 3-[(N-alkyl)ureido]propionic acid (2) can be prepared by the reaction of an alkyl ester of

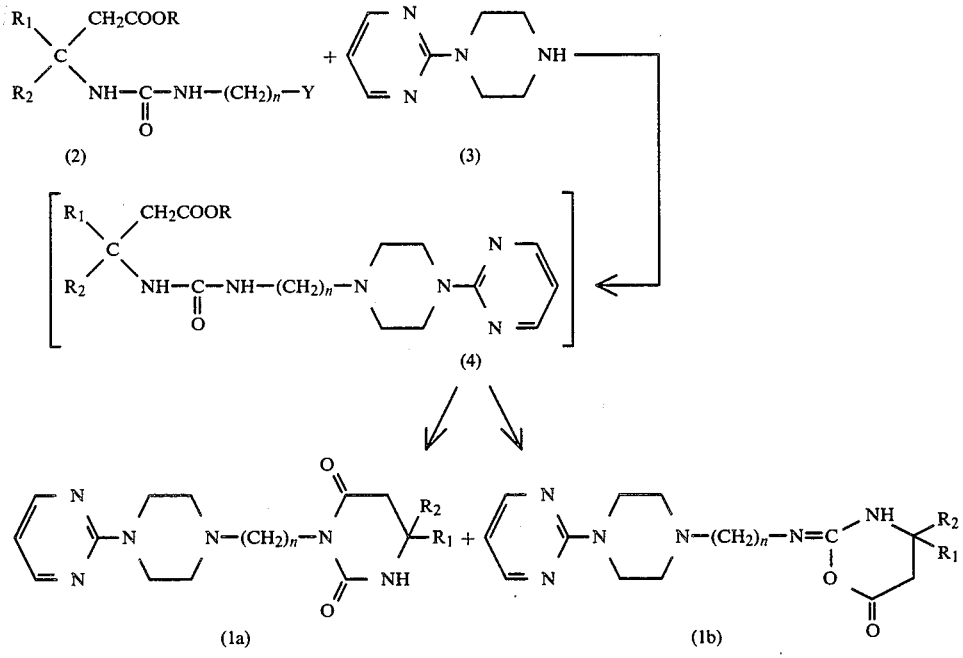

3-aminopropionic acid (5) with an alkyl isocyanate (6), containing a suitable leaving group as illustrated below. The symbols R, $R_1$, $R_2$, n and Y have the values previously described.

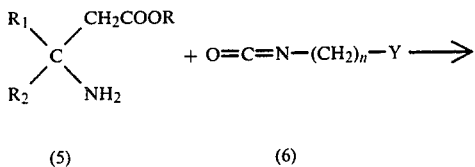

(5)  (6)

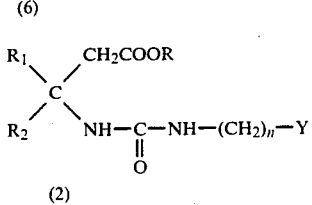

(2)

Approximately equimolar amounts of reactants (5) and (6) are employed. Inasmuch as both reactants are liquids at room temperature, the raction can be conducted by simple mixing. Preferably, however, the use of a suitable aprotic solvent is employed. Suitable aprotic solvents include chlorinated hydrocarbons, such as methylene chloride, ethylene chloride or carbon tetrachloride; aromatic hydrocarbons such as benzene or toluene; ethereal solvents such as diethylether, tetrahydrofuran or p-dioxane and esters of organic acids such as ethyl acetate.

The reaction is exothermic and can be conducted at room temperature employing suitable means for cooling. Depending upon the reactants utilized, their concentration and the particular solvents employed, the reaction can be conducted at temperatures ranging from −30° C. to ambient temperatures for periods of time ranging from 30 minutes to 3 hours. Preferably temperatures from −20° C. to 0° C. are employed, with reaction times ranging from 30 minutes to 1 hour. Removal of the solvents from the reaction mixture, generally via evaporation, leaves the desired alkyl esters of 3-[(N-alkyl)ureido]propionic acid, which can then be utilized in the manner previously indicated.

Alternatively, the alkyl esters of 3-[N-[ω-[4-(2-pyrimidinyl)-1-piperazinyl]alkyl]ureido]propionic acid (4) can be prepared via the nucleophilic condensation of an alkyl ester of 3-isocyanopropionic acid of formula (7), with an ω-[4-(2-pyrimidinyl)-1-piperazinyl]alkylamine (8) as shown below. The symbols R, $R_1$, $R_2$ and n have the same values previously assigned.

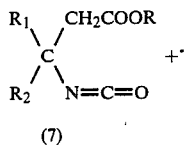

(7)

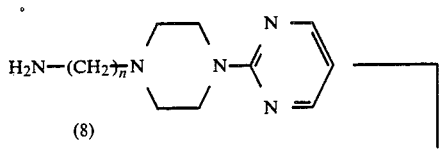

(8)

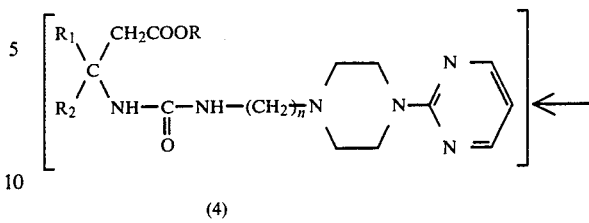

(4)

This nucleophilic condensation is preferably conducted using equimolar amounts of the alkyl esters of 3-isocyanopropionic acid (7) with the ω-[4-(2-pyrimidinyl)-1-piperazinyl]alkylamine (8) under essentially the same reaction conditions for the reaction previously described involving the converse functionalities, i.e., the reaction of an alkyl ester of 3-aminopropionic acid (5) with the alkyl isocyanate (6).

The compounds of formula (1) possess useful antianxiety properties. Anxiolytic properties are indicated using 5-$HT_{1A}$ in vitro receptor binding studies, see Middlemiss et al., Eur. J. Pharmacol., 90, 151–3 (1983) and Glaser et al., Arch. Pharmacol., 329, 211–215 (1985). Additionally, the anxiolytic properties for the compounds described herein can be demonstrated in vivo, utilizing a rat licking test, which is a recognized animal model for anxiety utilized by those skilled in the art, see Vogel et al., Psychopharmacologia, 21, 1–7 (1971).

The compounds of this invention can be administered either orally, subcutaneously, intravenously, intramuscularly, intraperitoneally or rectally. The preferred route of administration is oral. The amount of compound to be administered can be any effective amount and will, of course, vary depending upon the patient, the mode of administration and the severity of the anxiety to be treated. Repetitive daily administration of the compounds may be desirable, and will vary depending upon the patient's condition and the particular mode of administration.

For oral administration, an anxiolytic effective amount of compound can range from 0.005 to 10 mg/kg of patient body weight per day, preferably from 0.05 to 5 mg/kg of patient body weight per day. The preferred antianxiety dose of the compounds of formula (1a) is about 0.4 mg/kg of patient body weight per day. Pharmaceutical compositions in unit dose form contain from 1 to 50 mg of active ingredient and can be administered one or more times per day.

The compounds can be formulated into solid or liquid preparations such as capsules, pills, tablets, lozenges, melts, powders, solutions, suspensions or emulsions. Solid dosage unit forms generally employed include capsules or tablets. Capsules can be of the ordinary gelatin type which contain additional excipients such as, surfactants, lubricants and inert fillers such as lactose, sucrose and cornstarch. Tablets containing compounds of formula (1) can be formed with conventional tablet bases such as lactose, sucrose, and cornstarch in combination with binders, such as acacia, cornstarch or gelatin, disintegrating agents such as potato starch or alginic acid, and lubricants such as stearic acid or magnesium stearate.

For parenteral administration, an anxiolytic effective amount of compound ranges from about 0.005 to 10 mg/kg of patient body weight per day, preferably from about 0.05 to 5 mg/kg of patient body weight per day. A parenteral composition in unit dose form contains from 0.1 mg to 10 mg of active ingredient and can be administered one or more times daily.

The compounds may be administered as injectable dosages of a solution or a suspension of the compound in a physiologically acceptable diluent with or without a pharmaceutical carrier. Suitable diluents or carriers include sterile liquids such as water or oils, with or without the addition of surfactants or other pharmaceutically acceptable adjuvants. Illustrative of various oils that can be employed in the practice of this invention are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solution.

The following examples illustrate the preparation of representative compounds employed in the practise of this invention, but are not intended to limit the invention in any way thereto.

EXAMPLE I

1-[4-[4-(2-Pyrimidinyl)-1-piperazinyl]butyl]-tetrahydro-6,6-dimethylpyrimidine-2,4-dione

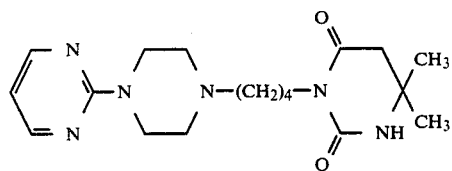

2-[4-[4-(2-Pyrimidinyl)-1-piperazinyl]butylimino]-tetrahydro-4,4-dimethyl-6H-1,3-oxazine-6-one

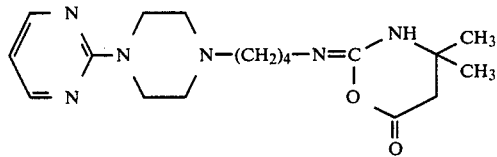

4-Bromobutylisocyanate

A solution of 5-bromopentanoic acid (36.2 g) in thionylchloride (15.7 ml) is stirred for 2 hours at room temperature and the excess thionyl chloride removed by evaporation. The acid chloride residue is dissolved in acetone (50 ml) and the solution slowly added to a stirred suspension of sodium azide (13 g) in water (15 ml) at 0° C. After stirring for an additional 30 minutes, the reaction mixture is extracted with ether. The ether layer is washed several times with a saturated sodium bicarbonate solution, dried over MgSO4, and evaporated to yield 5-bromopentanoyl azide (29 g) as an oil. A solution of the acid azide in benzene is refluxed for 2 hours and then distilled to yield 4-bromobutylisocyanate, bp 110° C./15 mm (15.1 g).

Ethyl 3-[(4-Bromobutyl)aminocarbonylamino]-3-methylbutanoate

A solution of 4-bromobutylisocyanate (15.1 g) in methylene chloride (50 ml) is added to a stirred solution of ethyl 3-amino-3-methylbutanoate (12.3 g), dissolved in methylene chloride (50 ml) at −20° C. The mixture is stirred for 30 minutes at −20° C. and then for an additional 2 hours at room temperature. Evaporation of the solvent yields a residue of ethyl 3-[(4-bromobutyl)aminocarbonylamino]-3-methylbutanoate (26 g).

1-[4-[4-(2-Pyrimidinyl)-1-piperazinyl]butyl]-tetrahydro-6,6-dimethylpyrimidine-2,4-dione and 2-[4-[4-(2-Pyrimidinyl)-1-piperazinyl]butylimino]tetrahydro-4,4-dimethyl-6H-1,3-oxazine-6-one A mixture of ethyl 3-[(4-bromobutyl)aminocarbonylamino]-3-methylbutanoate (3.21 g), 1-(2-pyrimidinyl)piperazine (1.64 g), potassium carbonate (1.38 g) and dimethylformamide (50 ml) is heated at 100° C. for 3 hours, left overnight at room temperature, filtered, and evaporated to dryness. The residue is chromatographed on silica gel using a mixture of ethyl acetate-ethanol (90:10) as the eluent to yield 2-[4-[4-(2-pyrimidinyl)-1-piperazinyl]butylimino]-tetrahydro-4,4-dimethyl-6H-1,3-oxazine-6-one, m.p. 124°–6° C. when crystallized from aqueous methanol (Rf 0.3) and 1-[4-[4-(2-pyrimidinyl)-1-piperazinyl]butyl]tetrahydro-6,6-dimethylpyrimidine-2,4-dione, as an oil (Rf 0.2).

A solution of the pyrimidine-2,4-dione in ether is treated with ethereal oxalic acid to yield the corresponding oxalate salt having an m.p. 128°–130° C. when crystallized from isopropanol.

EXAMPLE II

1-[4-[4-(2-Pyrimidinyl)-1-piperazinyl]butyl]-tetrahydro-6,6-dimethylpyrimidine-2,4-dione

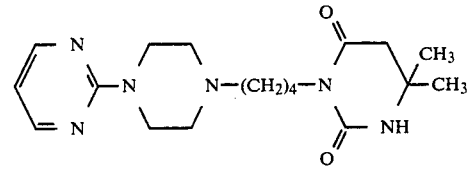

and

2-[4-[4-(2-Pyrimidinyl)-1-piperazinyl]butylimino]-tetrahydro-4,4-dimethyl-6H-1,3-oxazine-6-one

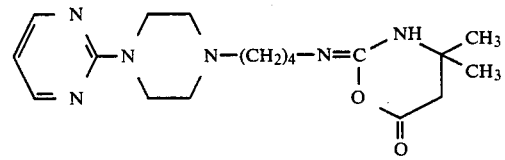

2-Ethoxycarbonyl-1,1-dimethylethylisocyanate

A solution of trichloromethyl chloroformate (4.1 g) in methylene chloride (15 ml) is slowly added to a stirred mixture of ethyl-3-amino-3-methylbutanoate (3 g), triethylamine (6.6 g) and methylene chloride (30 ml) at 5° C. The mixture is stirred overnight at room temperature, refluxed for 3 hours, cooled and anhydrous ether added thereto. The precipitated triethylamine hydrochloride is filtered and the filtrate evaporated to yield 2-ethoxycarbonyl-1,1-dimethylethylisocyanate as an oil (3.5 g).

Ethyl 3-[4-[4-(2-pyrimidinyl)-1-piperazinyl]butyl]aminocarbonylamino-3-methylbutanoate A solution of the above isocyanate (3.5 g) in methylene chloride (10 ml) is added to a stirred solution of 4-[4-(2-pyrimidinyl)-1-piperazinyl]butylamine (4.15 g) in methylene chloride (10 ml) at room temperature. A slight exothermic reaction is observed. After stirring for 30 minutes the methylene chloride is evaporated, the residue is dissolved in a one Normal solution of HCl (50 ml), and the solution is extracted with ethyl acetate. The aqueous layer is made alkaline with saturated potassium carbonate and extracted with ether. Distillation of the dried ether extract yields 3-[4-[4-(2-pyrimidinyl)-1-piperazinyl]butyl]aminocarbonylamino-3-methylbutanoate as a syrup (5.4 g).

1-[4-[4-(2-pyrimidinyl)-1-piperazinyl]butyl]-tetrahydro-6,6-dimethylpyrimidine-2,4-dione and 2-[4-[4-(2-pyrimidinyl)-1-piperazinyl]butylimino]-tetrahydro-4,4-dimethyl-6H-1,3-oxazine-6-one A solution of potassium tert butoxide (1 g) in ethanol (5 ml) is added to a solution of ethyl 3-[4-[4-(2-pyrimidinyl)-1-piperazinyl]butyl[aminocarbonylamino-3-methylbutanoate (5.4 g) in ethanol (10 ml) and the stirred mixture refluxed for 30 minutes. The ethanol is evaporated, the residue is treated with water (50 ml) and the oil that forms is extracted with methylene chloride. Evaporation of the combined, dried methylene chloride extracts yields a syrup which partially crystallizes. The syrup is treated with ether and the crystals are removed by filtration (2 g). A solution of the crystals in aqueous methanol is treated with charcoal, filtered and is allowed to recrystallize to yield 2-[4-[4-(2-pyrimidinyl)-1-piperazinyl]butylamino]-tetrahydro-4,4-dimethyl-6H-1,3-oxazine-6-one, m.p. 124°–6° C. (1 g).

Evaporation of the ether solution leaves a syrup (2 g) which is chromatographed on silica gel to yield 1-[4-[4-(2-pyrimidinyl)-1-piperazinyl]butyl]-tetrahydro-6,6-dimethylpyrimidine-2,4-dione, as an oil. Treatment of the oil with ethereal oxalic acid gives the oxalate salt having an m.p. 128°–30° C.

EXAMPLE III

In vitro Determination of Anxiolytic Properties via 5-HT$_{1A}$ Binding

Radioligand binding studies of the 5-HT$_{1A}$ recognition sites are conducted in the following manner. Male normotensive Sprague-Dawley rat frontal cortex is dissected, frozen in liquid nitrogen and stored at −20° C. until needed. Tissues from 4–8 rats are pooled and homogenized in 70 vol Tris-HCl buffer (50 mM, pH 7.7), using a kinematica Polytron (setting $\frac{2}{3}$ max speed, 20 sec). The homogenate is centrifuged (36500×g for 10 min), the pellet re-homogenised in the same volume of buffer and the process is repeated two more times. Between the second and third centrifugations the tissue homogenate is incubated at 37° C. for 10 min. The final pellet is suspended in the same volume of Tris buffer containing 10M pargyline, 5.7 mM CaCl$_2$ and 0.1% ascorbic acid. This suspension is incubated for 10 min at 37° C. and then stored on ice until used in the binding assay.

Tissue homogenate (0.7 ml), radioactive ligand (0.1 ml) and the appropriate concentration of test compound (0.1 ml), together with buffer to a final volume of 1 ml are incubated at 37° C. for 15 min. Incubations are terminated by rapid filtration through Whatman GF/B filters followed by three 5 ml washes with ice-cold Tris-HCl buffer (50 mM, pH 7.0). Radio-activity is measured following extraction into Aquasol-Z (NEN) at an efficiency of 45–50%. The radioligand used to label the 5-HT$_{1A}$ recognition sites and its concentration is [$^3$H]-8-hydroxy-2-(di-n-propylamino)-tetralin, [$^3$H]-8-OH-DPAT, 1 mM.

Following essentially the above procedure, the compounds 1-[4-[4-(2-pyrimidinyl)-1-piperazinyl]butyl]-tetrahydro-6,6-dimethylpyrimidine-2,4-dione, (Compound A), and 2-[4-[4-(2-pyrimidinyl)-1-piperazinyl]-butylamino]-tetrahydro-4,4-dimethyl-6H-1,3-oxazine-6-one, (Compound B) are tested. The results are expressed as pIC$_{50}$ (log$_{10}$ concentration of test compound which inhibits specific binding by 50%).

| Test Compound | 5-HT$_{1A}$ Binding Affinity Rat Brain cortex |
| --- | --- |
| Compound A | 6.94 |
| Compound B | 6.32 |
| Buspirone | 7.52 |

We claim:

1. A 4-(2-pyrimidinyl)-1-piperazinyl heterocyclic carbonyl derivative having the formula:

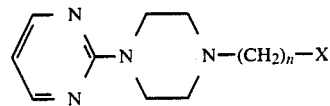

wherein n is an integer of from 2 to 5; X is the radical

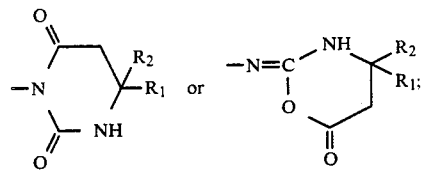

R$_1$ and R$_2$ are each methyl or when taken together form a tetramethylene or pentamethylene ring; and the pharmaceutically acceptable acid addition salts thereof.

2. A compound according to claim 1 wherein X is the radical

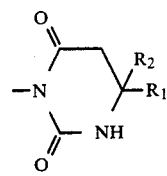

3. A compound according to claim 1, which is 1-[4-[4-(2-pyrimidinyl)-1-piperazinyl]butyl]-tetrahydro-6,6-dimethylpyrimidine-2,4-dione and the pharmaceutically acceptable salts thereof.

4. A compound according to claim 1 wherein X is the radical

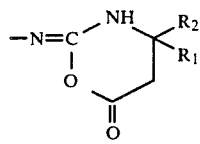

5. A compound according to claim 1, which is 2-[4-[4-(2-pyrimidinyl)-1-piperazinyl]butylimino]-tetrahydro-4,4-dimethyl-6H-1,3-oxazine-6-one and the pharmaceutically acceptable salts thereof.

6. A process for the preparation of a 4-(2-pyrimidinyl)-1-piperazinyl heterocyclic carbonyl derivative according to claim 1 which comprises reacting an alkyl ester of 3-[(N-alkyl)ureido]propionic acid having the formula

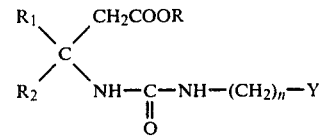

wherein n, $R_1$ and $R_2$ are as described in claim 1, R is lower alkyl group and Y is an appropriate leaving group, reacting said propionic acid with 1-(2-pyrimidinyl)piperazine to form an alkyl ester of 3-[N-[ω-[4-(2-pyrimidinyl)]-1-piperazinyl]alkyl]ureido]propionic acid; cyclizing said alkyl ester of (2-pyrimidinyl)-1-piperazinyl]alkyl]ureido]propionic acid, and isolating the desired 4-(2-pyrimidinyl)-1-piperazinyl heterocyclic carbonyl derivative therefrom.

7. A method for relieving the symptoms of anxiety in a patient in need thereof, which comprises the administration to said patient of an anxiolytic effective amount of a compound of claim 1.

8. An anxiolytic composition comprising an anxiolytic effective amount of a compound of claim 1, or a pharmaceutically acceptable salt thereof, in combination with a pharmaceutically acceptable carrier or diluent.

* * * * *